United States Patent [19]

Yuen

[11] Patent Number: 4,908,023

[45] Date of Patent: Mar. 13, 1990

[54] SYRINGE ASSEMBLY

[76] Inventor: Frank Yuen, 110-20 71st St., Forest Hills, N.Y. 11375

[21] Appl. No.: 232,014

[22] Filed: Aug. 15, 1988

[51] Int. Cl.$^4$ ............................................. A61M 5/32
[52] U.S. Cl. ................................... 604/118; 604/110; 604/192
[58] Field of Search ............... 604/198, 192, 263, 110, 604/199, 200, 194, 209, 210, 211, 220, 224, 228

[56] References Cited

U.S. PATENT DOCUMENTS

| | | | |
|---|---|---|---|
| 3,828,775 | 8/1974 | Armel | 604/200 |
| 4,573,976 | 3/1986 | Sampson et al. | 604/198 |
| 4,631,057 | 12/1986 | Mitchell | 604/198 |
| 4,655,751 | 4/1987 | Harbaugh | 604/198 |
| 4,666,435 | 5/1987 | Braginetz | 604/198 |
| 4,693,708 | 9/1987 | Wander et al. | 604/198 |
| 4,710,179 | 12/1987 | Haber et al. | 604/211 |
| 4,743,233 | 5/1988 | Schneider | 604/192 |
| 4,747,837 | 5/1988 | Hauck | 604/198 |
| 4,752,290 | 6/1988 | Schramm | 604/198 |
| 4,801,295 | 1/1989 | Spencer | 604/198 |
| 4,826,491 | 5/1989 | Schramm | 604/198 |
| 4,840,185 | 6/1989 | Hernandez | 128/763 |

FOREIGN PATENT DOCUMENTS 0958636  5/1964  United Kingdom .

Primary Examiner—C. Fred Rosenbaum
Assistant Examiner—Mark O. Polutta
Attorney, Agent, or Firm—Collard, Roe & Galgano

[57] ABSTRACT

A syringe assembly having a hollow barrel, a plunger and a hypodermic needle and is discardable after a single use. The hypodermic needle has a first end fixedly secured to and in communication with the barrel and has a free end for the discharge of medication therefrom upon the downward movement of the plunger within the barrel. The barrel is covered by a two-part hollow cylindrical sheath having a first part extending, when in a first position, along the barrel a distance allowing at least the partial exposure of the hypodermic needle and having a second part extending, when in the first position, a distance beyond the free end of the needle to substantially cover the same. The second part of the sheath has one end coupled to the first part by a breakable joint which can be broken so that the second part may be discarded prior to use. The needle includes a ratchet system to allow the first part of the sheath to be extended over the hypodermic needle after the syringe has been used which ratchet system includes a locking pawl to permanently prevent movement of the sheath upwardly along the syringe barrel.

3 Claims, 2 Drawing Sheets

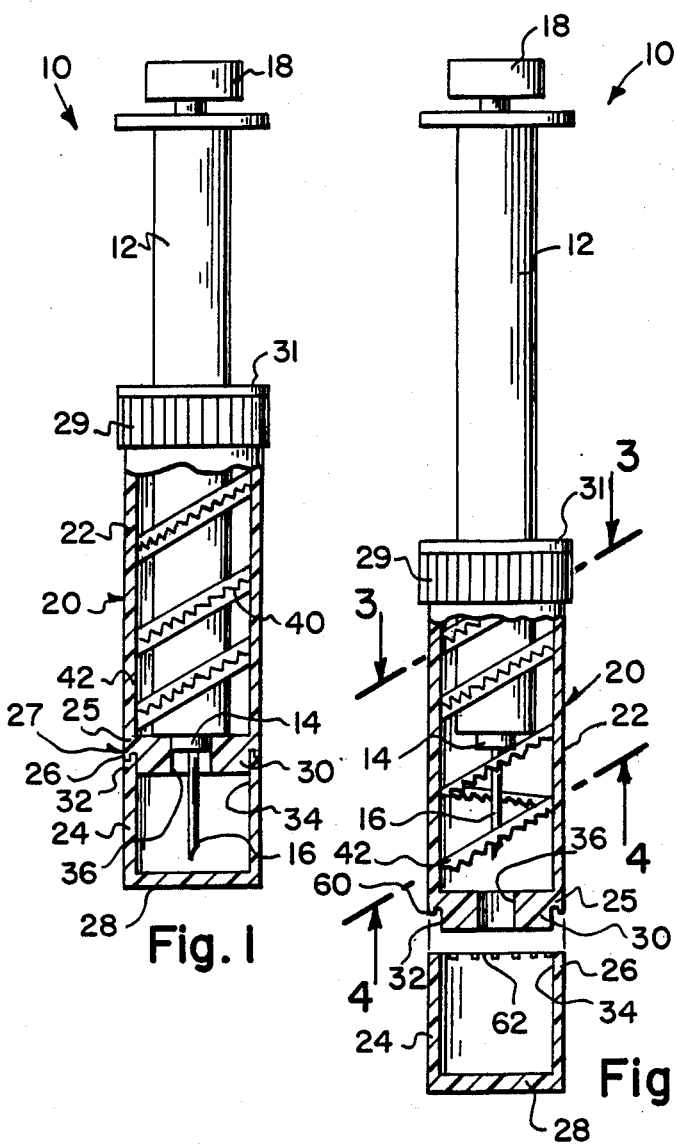
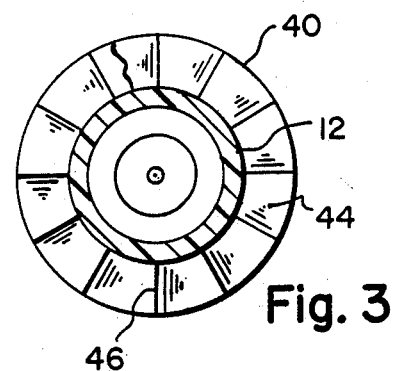
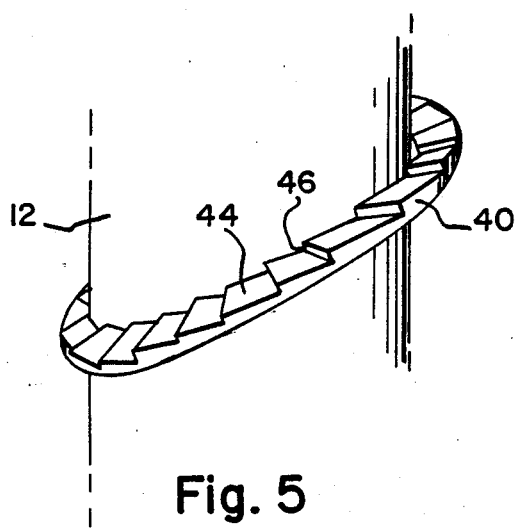

SYRINGE ASSEMBLY

BACKGROUND OF THE INVENTION

1. Field of the Invention

This invention relates to a syringe assembly and, more particularly, to a disposable hypodermic syringe and needle combination which has a two-part sheath including a first part which is extendable to prevent accidents, abuse and reuse of the syringe assembly after the initial use.

2. Description of the Prior Art

Various types of syringe assemblies for receiving and dispensing medication as well as other materials have been known. In general, the medication or other materials are introduced into the hollow barrel portion either by receiving the same through the needle which communicates with the barrel interior, or by means of a frangible container, such as an ampule, which is placed within the hollow barrel. Applying pressure to the plunger causes the medication or other material to be expressed through the hollow needle.

Hypodermic syringe assemblies are often used for administering medication to patients suffering from infectious diseases. Therefore, it has been considered of great importance in the art to avoid accidents, where doctors, nurses, or other persons suffer puncture wounds from use of hypodermic needles. Presently, the safe disposal of used syringes and needles is considered a serious problem in the art, particularly in light of the recent spread of acquired immune deficiency syndrome (AIDS), and the wide-spread abuse of syringes and needles by addicts for administering illicit drugs.

In order to prevent the incidence of puncture wounds which are sometimes accidentally self-inflicted by doctors and nurses, there has been a need to provide a simple method for immediately covering the hypodermic needle after use. Furthermore, there has been a need to insure that the needles are not re-used and therefore it has been found expedient to develop a means for locking a protective extension over the hypodermic needle after use to protect medical personnel and to prevent the re-use of the disposable syringe.

U.S. Pat. No. 4,702,738 addresses this problem by providing a disposable hypodermic syringe with a retractable and lockable sheath. Other patents, such as U.S. Pat. No. 4,356,822, also disclose a syringe assembly having a sheath which can be extended to cover the needle but which cannot be locked in this extended position. In addition, U.S. Pat. Nos. 4,237,882, 4,416,663, 4,573,972, 4,731,059, 4,139,009 and 3,967,621 all disclose syringe assemblies with various means for protecting the needle either before or after use.

SUMMARY OF THE INVENTION

It is an object of the present invention to provide a disposable hypodermic syringe assembly wherein the needle is protected before and after use to prevent accidents involving the used needle.

It is another object of the invention to provide a disposable hypodermic syringe assembly wherein the needle is protected before use by a removable extension of a protective sheath surrounding the syringe barrel wherein the needle is permanently and irreversibly concealed by the sheath after use so as to prevent abuse by users of illicit drugs.

It is a further object of the present invention to provide such a syringe assembly which is adapted for use in accordance with standard accepted medical procedures.

Accordingly, these and other objects are achieved by a syringe assembly of the type which is discardable after a single use and which includes a hollow barrel for holding medication. A plunger is mounted within the barrel and the hypodermic needle is fixedly secured to and in communication with the barrel. The hypodermic needle has a free end for the discharge of the material or medication therefrom upon the downward movement of the plunger within the barrel. A two-part, hollow cylindrical sheath is mounted on an external surface of the barrel and has a first part extending along the barrel when in a first upper position a distance allowing at least the partial exposure of the hypodermic needle. The sheath has a second part extending in the first position a distance beyond the free end of the needle to substantially cover the same. The second part of the hollow cylindrical sheath has one end coupled to the first part by a separable joint, which may be in the form of a perforated joint, and has a closed free end for enclosing the free end of the hypodermic needle prior to use. In order to use the syringe assembly, the second part of the sheath is removed from the first part of the sheath by breaking the joint therebetween by a twisting or pulling action.

In order to allow the first part of the sheath to extend downwardly along the syringe barrel, a ratchet system is included which has outwardly extending teeth having generally upwardly facing engagement surfaces formed on the external surfaces of the barrel and extending longitudinally thereon. A locking pawl or series of locking pawls or matching teeth are formed on an inner cylindrical surface of the sheath. The locking pawls or teeth are operatively coupled to the outwardly extending teeth formed on the external surface of the barrel. These locking pawls or locking teeth are slidable over the outwardly extending teeth upon downward movement of the sheath along the barrel, while upward movement is prevented by the locking pawl or the teeth on the sheath lockingly engaging the outwardly extending teeth of the ratchet.

In addition, it has been found advantageous to extend the ratchet system in a spiral fashion around the external surface of the barrel so that the sheath may be "unscrewed" when placing it in an extended position after using the needle. To facilitate this twisting or screwing action, the sheath is provided with a knurled outer surface adjacent the upper end thereof. In addition, it has been found that making the sheath transparent facilitates the introduction and dispensing of medication from the syringe.

While the locking pawl can be made in the form of a deflectable plastic extension on the inner surface of the sheath, it can also be formed from a series of inwardly extending teeth having generally downwardly facing surfaces thereon adapted to engage the corresponding upwardly facing surfaces on the outwardly extending teeth of the ratchet of the needle barrel. The outwardly extending ratchet teeth have a first surface facing upwardly on the barrel and extend outwardly of the barrel in the radial direction. These teeth spiral around the outside of the barrel and the inside of the sheath in a stepped fashion.

These and other objects and advantages of the present invention will become apparent from the following description of the accompanying drawings, which disclose several embodiments of the present invention. It is to be understood that the drawings are to be used for the purpose of illustration only, and not as a definition of the invention.

BRIEF DESCRIPTION OF THE DRAWINGS

In the drawings, wherein similar reference characters denote similar elements throughout the several views:

FIG. 1 is a side view of the syringe assembly of the present invention partly in cross section, the side view showing the two-part protective sheath prior to use;

FIG. 2 is a side view of the syringe assembly, partially in cross-section, with the protective sheath extended to cover the needle and with the second part of the two-part sheath removed.

FIG. 3 is a cross sectional view taken along the lines 3—3 of FIG. 2;

FIG. 4 is a cross sectional view taken along the lines 4—4 of FIG. 2;

FIG. 5 is a partial isometric view of a section of the ratchet means formed on the syringe barrel;

DESCRIPTION OF THE PREFERRED EMBODIMENTS

Figure 6:
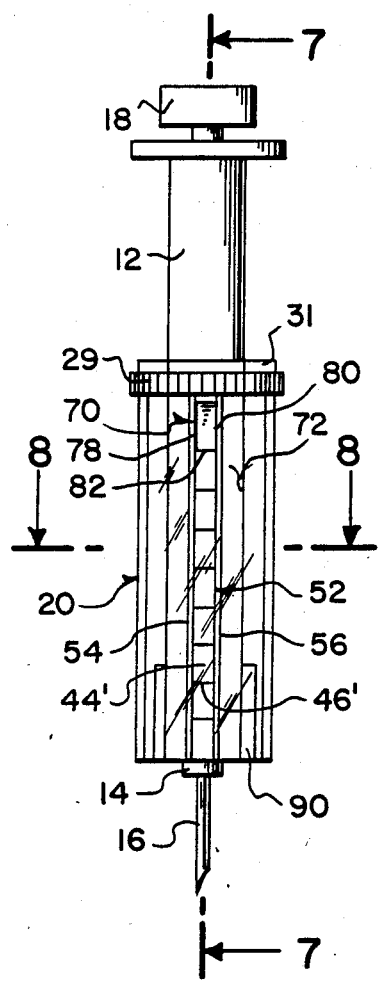
FIG. 6 is a side view of a second embodiment of the syringe assembly partially in cross-section with the lower part of the sheath removed.

Referring now to FIG. 1, there is shown a disposable syringe assembly denoted as 10, including a hollow cylindrical barrel 12 which in the usual form is substantially cylindrical and terminates in a needle support 14 which terminates in a hypodermic needle 16. As is well known, the needle 16 is hollow and is in communication with the hollow interior of barrel 12. A plunger 18 is housed within the interior of cylindrical barrel 12 and upon downward movement thereof expels the medication or material from hypodermic needle 16.

A two-part sheath 20 is mounted around the end of the barrel adjacent hypodermic needle 16. Sheath 20 has a predetermined diameter larger than the external diameter of barrel 12. The barrel 12 is at least partially received within the sheath 20. Two-part sheath 20 has a first part 22 surrounding the barrel 12 when in a first raised position as shown in FIG. 1. The sheath 20 also has a second part 24 having a first end 26 thereof attached to the lower end 25 of first part 22 and prior to use is adjacent needle support 14. Prior to use, second part 24 is joined to first part 22 by a separable joint 27, optionally via perforations in the wall of sheath 20 which perforations, as is described below, extend completely around the circumference of sheath 20. First part 22 also includes a knurled or textured upper portion 29 to facilitate gripping the sheath when moving it downward along barrel 12.

Second part 24 includes a closed free end 28 adjacent to free end of needle 16. Closed free end 28 prevents contact with and the contamination of needle 16 prior to using disposable syringe assembly 10. The lower end 25 of first part 22 includes a downwardly extending boss 30 having an outer surface 32 adapted to support inner surface 34 of second part 24 of sheath 20. Boss 30 is generally annular in shape and includes a central opening 36 adapted to allow the needle 16 to extend therethrough but prevent the accidental entry of a finger tip after removal of second part 24 and the extension of sheath 20 to a second position covering the tip of needle 16, as shown in FIG. 2.

Referring to FIGS. 1-4, there is shown a ratchet system comprising complementary ratchet teeth 40 and 42 formed on the external surface of barrel 12 and on the internal surface of part 22 of sheath 20, respectively. Ratchet teeth 40 face upwardly and may be disposed longitudinally along the shaft of barrel 12 in a spiral fashion, starting at a predetermined distance upward on barrel 12 and extending downwardly towards the end of barrel 12 including needle 16. Similarly, radially inwardly extending and downwardly facing teeth 42 may be positioned around the internal surface of sheath 20 and spiral in like fashion downwardly until reaching end 25 of first part 22 of sheath 20.

Each tooth 40 includes a generally upwardly facing surface 44 terminating in a generally upwardly facing surface 46 which extends generally perpendicularly to surface 44 and radially towards barrel 12. Likewise, teeth 42 have complementary surfaces 48 which face generally downwardly and include surfaces 50, which extend generally perpendicularly to surface 48 of sheath 20. It can be seen that the ratchet teeth allow sliding motion in the downward direction along barrel 12 between inclined surfaces 44 and 48. Upward movement along barrel 12 is prevented by the engagement of generally perpendicular radially extending surfaces 46 and 50.

Referring to FIG. 5, there is shown the ratchet system as described above, formed on barrel 12. The teeth 40 are formed thereon as described above, and are adapted to mate with the teeth 42 as shown in cross section in FIG. 4.

Referring to FIG. 2, there is shown syringe assembly 10 in the area of joint 27 just after lower part 24 of sheath 20 has been broken off of and separated from upper part 22. This separation was accomplished by breaking tabs 60 in upper part 22 from tabs 62 on lower part 24 along a line of weakened material formed therebetween. The line of weakened material is merely made by having the sheath wall along this line made of much thinner material or with the wall partially cut to form the perforations when molding the sheath. Thus, part 22 may be separated from part 24 by a twisting or flexing motion. Because wall 72 is thinner or cut but not pierced, the sterility of the needle is maintained.

Referring to FIGS. 6-9, there is shown a second embodiment of syringe assembly 10 which utilizes a ratchet system using a ratchet track member 52, but instead of teeth 42, this embodiment has at least one pawl 70 formed in the wall 72 of sheath 20. Pawl 70 may be formed as an inwardly extending tab element 74 having a free end 76 and sides 78 and 80, all of which initially are formed from a part of wall 72 of sheath 20. To form tab element 74, wall 72 is cut in the shape of a "U" with end 82 of tab 74 still attached to wall 72. Free end 76 is then inwardly deformed to form pawl 70.

It can be seen that walls 54 and 56 of track member 52 serve to engage sides 78 and 80 of pawl 70 and guide the pawl when sheath 20 is moved downwardly along cylindrical barrel 12. If track member 52 extends in a straight line longitudinally down barrel 12, then the engagement of walls 54 and 56 with sides 78 and 80 of pawl 70 serves to prevent rotation of the sheath 20 with respect to barrel 12.

Figure 7:
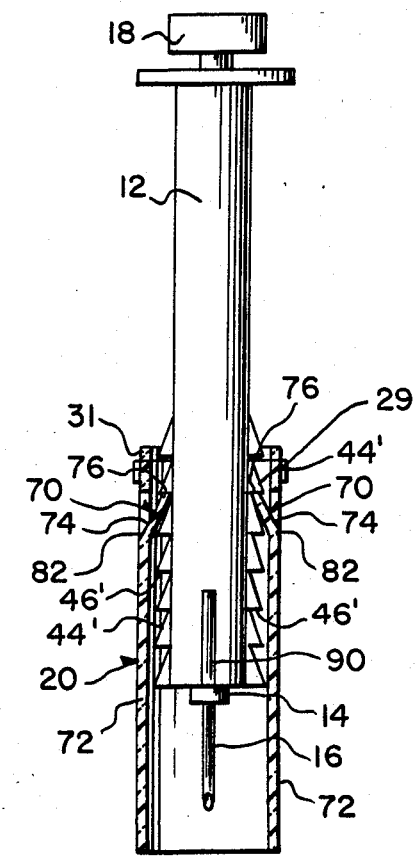
FIG. 7 is a side view of a second embodiment of the syringe assembly of the present invention partially in cross-section with the sheath extended.
Figure 8:
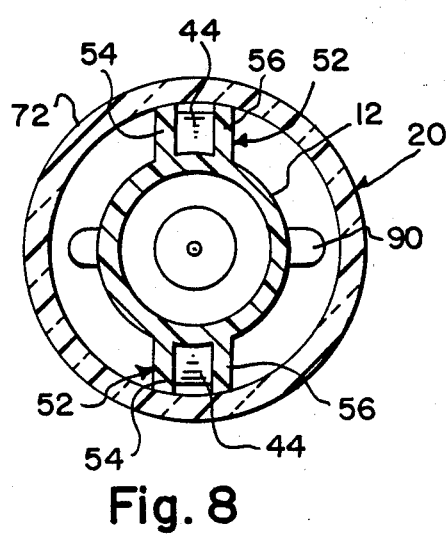
FIG. 8 is a cross-sectional view of the syringe assembly of FIG. 6 along the lines 8—8.
Figure 9:
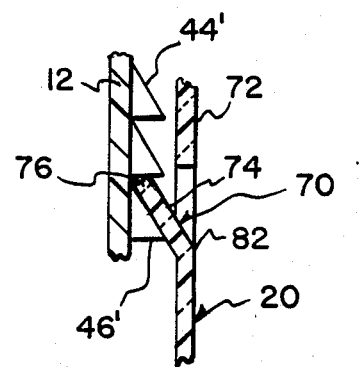
FIG. 9 is an enlarged cross-sectional view of the engagement between the locking pawl and ratchet shown in FIG. 7.

Referring to FIG. 7, it can be seen that free end 76 of pawl 70 faces upwardly along barrel 12 so that it may slide over surfaces 44' of track member 52 when sheath 20 is moved downwardly along barrel 12 but engages surface 46', thereby preventing upward movement of sheath 20 once moved to a second position with respect to barrel 12 covering needle 16.

While only two of the longitudinally extending ratchet tracks 52 are shown, it can be seen that three or even more devices may be spaced around the periphery of barrel 12, and that more than one pawl can be formed in sheath 20 and engage each ratchet track 52 to provide added resistance to the upward movement of sheath 20 with respect to barrel 12.

In order to ensure that the sheath 20 cannot be removed from the bottom end of syringe barrel 12 after use stop plate 31 is provided in both the embodiments shown in FIG. 1-5 and 6-9. Stop plate 31 is formed as an integral inwardly extending ledge on top of knurled surface 29 of sheath 20. Stop plate 31 has a circular opening capable of allowing barrel 12 to slide therethrough. In the embodiment of FIGS. 1-5, stop 31 engages the first tooth 40 of the ratchet system formed integrally with syringe barrel 12 threby preventing further downward motion. In the embodiment of FIGS. 6-9, stop 90 is integrally formed on the lower portion of syringe barrel 12 and engages stop plate 31 when the sheath 20 is moved into a lower position covering needle 16. Thus, stop 31 and 90 prevent further downward movement of sheath 20 which is thus locked from movement with respect to barrel 12.

To use the disposable syringe assembly 10, one grasps part 24 of sheath 20 by knurled portion 29 of first part 22 and applies a twisting motion to second part 24, thereby tearing the tabs 60, 62 in perforated joint 27. At this point, part 24 may be discarded, thus exposing needle 16. Medication is aspirated into barrel 12 of syringe assembly 10 by the movement of plunger 18 in the upward direction. After injecting the medication, knurled section 29 of sheath 20 is grasped and the sheath is moved downwardly (with the embodiment of FIGS. 1-5 by turning clockwise), thus causing the movement of first part 22 from the first upward position until stop 31 on sheath 20 engages the top ratchet tooth 40 in the second lower position where the free end 25 of the section 22 extends beyond the free end of needle 16. If the embodiment shown in FIGS. 6-9 is used, then no twisting movement is required since the sheath may be slid axially down along barrel 12 until encountering stops 90. At this point, the sheath 20 is locked in position over the needle 16 by the engagement of surfaces 46 and 50 or 46' and 76, thereby preventing accidental injury with the needle or the undesired re-use of the syringe assembly.

While several of the embodiments and examples of the present invention have been illustrated and described, it is obvious that many changes and modifications may be made thereunto, without departing from the spirit and scope of the invention.

What is claimed is:

1. A syringe assembly comprising:
   a hollow barrel;
   a plunger means mounted within said barrel;
   a hypodermic needle having a first end fixedly secured to and in communication with said barrel and having a free end for the discharge of material therefrom upon downward movement of said plunger within said barrel;
   a hollow cylindrical sheath mounted to the barrel and extendable from a first retracted position exposing said hypodermic needle to a second position substantially covering said hypodermic needle;
   ratchet means including a continuous row of regularly spaced and aligned outwardly extending teeth formed on the external surface of said barrel and extending longitudinally thereon wherein said ratchet means extending longitudinally on said barrel follows a spiral path around the external cylindrical surface of said barrel; and
   locking pawl means extending radially inwardly from an inner cylindrical surface of said sheath, said locking pawl means operatively coupled to said outwardly extending teeth formed on the external surface of said barrel such that, upon movement of said sheath from said first retracted position to said second position, said locking pawl means continuously engages and slides over said teeth permitting movement of said sheath from said first position to said second position while movement from said second position to said first position is prevented by the continuous engagement of said locking pawl means with said outwardly extending teeth of said ratchet means.

2. The syringe assembly as set forth in claim 1, wherein said sheath has a textured outer surface adjacent an upper end thereof.

3. The syringe assembly as set forth in claim 1, wherein said sheath is transparent.

* * * * *